US009119983B2

(12) United States Patent
Rhea

(10) Patent No.: US 9,119,983 B2
(45) Date of Patent: Sep. 1, 2015

(54) HEART RATE BASED TRAINING SYSTEM

(71) Applicant: Icon Health & Fitness, Inc., Logan, UT (US)

(72) Inventor: Matthew Rhea, Logan, UT (US)

(73) Assignee: ICON Health & Fitness, Inc., Logan, UT (US)

( * ) Notice: Subject to any disclaimer, the term of this patent is extended or adjusted under 35 U.S.C. 154(b) by 219 days.

(21) Appl. No.: 13/652,576

(22) Filed: Oct. 16, 2012

(65) Prior Publication Data

US 2013/0123071 A1 May 16, 2013

Related U.S. Application Data

(60) Provisional application No. 61/559,878, filed on Nov. 15, 2011.

(51) Int. Cl.
*A63B 24/00* (2006.01)
*A63B 22/00* (2006.01)
(Continued)

(52) U.S. Cl.
CPC ............ *A63B 24/00* (2013.01); *A63B 22/0023* (2013.01); *A63B 22/0235* (2013.01); *A63B 24/0075* (2013.01); *A63B 24/0087* (2013.01); *A63B 22/0056* (2013.01); *A63B 22/0076* (2013.01); *A63B 22/0605* (2013.01); *A63B 22/0664* (2013.01); *A63B 22/203* (2013.01); *A63B 2024/0065* (2013.01); *A63B 2024/0093* (2013.01); *A63B 2220/836* (2013.01);

(Continued)

(58) Field of Classification Search
CPC ............... A63B 24/00; A63B 24/0075; A63B 24/0087; A63B 2230/20; A63B 2230/067; A63B 22/0023; A63B 22/0056; A63B 22/0076; A63B 22/0235; A63B 22/06205; A63B 22/0664; A63B 22/203
USPC ........................ 482/1–9, 51, 54, 57, 900–902
See application file for complete search history.

(56) References Cited

U.S. PATENT DOCUMENTS

| | | |
|---|---|---|
| 4,998,725 A | 3/1991 | Watterson et al. |
| 5,067,710 A | 11/1991 | Watterson et al. |

(Continued)

FOREIGN PATENT DOCUMENTS

WO 2011105914 9/2011

OTHER PUBLICATIONS

International Search Report, PCT/US2012/060630, mailed Mar. 29, 2013.

*Primary Examiner* — Glenn Richman
(74) *Attorney, Agent, or Firm* — Holland & Hart LLP

(57) ABSTRACT

Exercise systems and methods are provided that create and run exercise programs that are custom tailored to individual users. An exercise program for a specific user is based upon the user's average work heart rate and recovery heart rate. The exercise programs may include a series of workouts for the user to perform. Each workout requires the user to exercise at various intensity levels so that the user's heart rate moves between different predetermined target heart rate zones. The target heart rate zones are calculated from data relating to the user's average work heart rate and recovery heart rate. As the user's fitness level changes, the user's average work heart rate and recovery heart rate also change. Creation of new exercise programs uses the most current heart rate data to calculate the target heart rate zones, thereby continuously tailoring the exercise programs to the user.

17 Claims, 7 Drawing Sheets

(51) Int. Cl.
*A63B 22/02* (2006.01)
*A63B 22/06* (2006.01)
*A63B 22/20* (2006.01)

(52) U.S. Cl.
CPC ....... *A63B2225/50* (2013.01); *A63B 2230/067* (2013.01); *A63B 2230/208* (2013.01)

(56) References Cited

U.S. PATENT DOCUMENTS

| | | | |
|---|---|---|---|
| 5,512,025 A | 4/1996 | Dalebout et al. | |
| 5,803,870 A | 9/1998 | Buhler | |
| 5,879,270 A | 3/1999 | Huish et al. | |
| 6,059,692 A | 5/2000 | Hickman | |
| 6,193,631 B1 | 2/2001 | Hickman | |
| 6,312,363 B1 | 11/2001 | Watterson et al. | |
| 6,450,922 B1 * | 9/2002 | Henderson et al. | 482/8 |
| 6,458,060 B1 | 10/2002 | Watterson et al. | |
| 6,626,800 B1 | 9/2003 | Casler | |
| 6,687,535 B2 | 2/2004 | Hautala et al. | |
| 6,749,537 B1 | 6/2004 | Hickman | |
| 6,808,472 B1 | 10/2004 | Hickman | |
| 6,921,351 B1 | 7/2005 | Hickman et al. | |
| 6,997,852 B2 | 2/2006 | Watterson et al. | |
| 7,060,006 B1 | 6/2006 | Watterson et al. | |
| 7,166,062 B1 | 1/2007 | Watterson et al. | |
| 7,455,622 B2 | 11/2008 | Watterson et al. | |
| 7,510,509 B2 | 3/2009 | Hickman | |
| 7,549,947 B2 | 6/2009 | Hickman et al. | |
| 7,575,536 B1 | 8/2009 | Hickman | |
| 7,625,315 B2 | 12/2009 | Hickman | |
| 7,628,730 B1 | 12/2009 | Watterson et al. | |
| 7,637,847 B1 | 12/2009 | Hickman | |
| 7,645,213 B2 | 1/2010 | Watterson et al. | |
| 7,713,171 B1 | 5/2010 | Hickman | |
| 7,789,800 B1 | 9/2010 | Watterson et al. | |
| 7,857,731 B2 | 12/2010 | Hickman et al. | |
| 7,980,996 B2 | 7/2011 | Hickman | |
| 7,981,000 B2 | 7/2011 | Watterson et al. | |
| 8,360,785 B2 * | 1/2013 | Park et al. | 434/247 |
| 8,790,220 B2 * | 7/2014 | Karvonen | 482/8 |
| 2005/0124463 A1 | 6/2005 | Yeo et al. | |
| 2007/0281828 A1 * | 12/2007 | Rice | 482/4 |
| 2009/0270744 A1 | 10/2009 | Prstojevich et al. | |
| 2009/0312658 A1 * | 12/2009 | Thieberger et al. | 600/520 |

\* cited by examiner

HEART RATE BASED TRAINING SYSTEM

CROSS-REFERENCE TO RELATED APPLICATIONS

This application claims priority to and the benefit of U.S. Provisional Patent Application No. 61/559,878, filed on Nov. 15, 2011, and entitled HEART RATE BASED TRAINING SYSTEM, which is incorporated herein by reference in its entirety.

TECHNICAL FIELD

This disclosure relates generally to systems, methods, and devices for exercise. More particularly, the disclosure relates to an exercise training program that is based on an exerciser's heart rate.

BACKGROUND

Well designed cardiovascular exercise programs can make exercise more effective, efficient, and even enjoyable. There are numerous cardiovascular exercise programs available to help people in their efforts to reach their health and fitness goals, including increased cardiovascular fitness, weight loss, or improved performance in endurance sports. Various factors are considered when developing a cardiovascular exercise program, such as the type of exercise to be performed, how much work will be done, and at what intensity training will be most effective. The type of exercise performed is primarily a matter of individual preference. The amount of work done (e.g., the length of each exercise session) should be reasonable, typically less than 60 minutes per day, to avoid overuse injuries and reduce the likelihood that the exerciser will stop exercising.

One of the more challenging aspects to developing an effective cardiovascular exercise program is determining the appropriate intensity for the training. In order to improve the function of the cardiovascular system, an individual must experience sufficient stress during exercise to stimulate adaptations. If training intensity is too low, sufficient overload is absent; however, if training intensity is too high, risk of overuse injury, cardiovascular events, and cessation of exercise are elevated.

A variety of methods have been employed to determine exercise intensity levels. One method uses percentages of an exerciser's maximum heart. The exerciser's maximum heart rate is calculated based on the exerciser's age, such as by subtracting the exerciser's age from 220. The exerciser then exercises at various intensity levels so that his or her heart rate is equal to certain percentages (e.g., between 60-85%) of the exerciser's maximum heart rate. One readily recognizable limitation of such a system is the lack of individualization of the system to specific exercisers. For instance, not all 40 year old men have a maximum heart rate of 180 beat per minute (i.e., 220-40). One 40 year old man may be quite fit, while another is just beginning a training programming Generic exercise programs, including age-predicted maximum heart rate programs, fail to account for each exerciser's unique fitness level.

Various exercise devices include the ability to monitor an exerciser's heart rate and adjust the operating parameters based on the detected heart rate. For instance, U.S. Pat. No. 7,713,171 discloses an exercise device that monitors a user's heart rate and adjusts the operating parameters to maintain the user's heart rate at a constant rate. Similarly, U.S. Pat. No. 7,857,731 discloses an exercise device that monitors a user's heart rate and adjusts the operating parameters if the user's heart rate is too high. Other exercise devices that monitor and/or adjust operating parameters based on the user's heart rate are disclosed in U.S. Pat. No. 4,998,725, U.S. Pat. No. 5,067,710, U.S. Pat. No. 5,512,025, U.S. Pat. No. 5,803,870, U.S. Pat. No. 5,879,270, U.S. Pat. No. 6,059,692, U.S. Pat. No. 6,193,631, U.S. Pat. No. 6,626,800, U.S. Pat. No. 6,749,537, U.S. Pat. No. 6,808,472, U.S. Pat. No. 7,575,536, U.S. Pat. No. 7,637,847, U.S. Pat. No. 7,575,536, U.S. Pat. No. 7,625,315, U.S. Pat. No. 7,510,509, U.S. Pat. No. 7,980,996, U.S. Pat. No. 6,921,351, U.S. Pat. No. 7,549,947, U.S. Pat. No. 6,312,363 U.S. Pat. No. 7,166,062, U.S. Pat. No. 7,060,006, U.S. Pat. No. 6,458,060, U.S. Pat. No. 6,997,852, U.S. Pat. No. 7,628,730, U.S. Pat. No. 7,789,800, U.S. Pat. No. 7,455,622, U.S. Pat. No. 7,645,213, and U.S. Pat. No. 7,981,000.

SUMMARY OF THE INVENTION

In one aspect of the disclosure, an exercise system includes a movable element that is movable in the performance of an exercise.

In another aspect that may be combined with any of the aspects herein, the movable element has at least one selectively adjustable operating parameter.

In another aspect that may be combined with any of the aspects herein, the exercise system includes a controller that adjusts the at least one selectively adjustable operating parameter of the movable element in order to increase or decrease the intensity of the exercise and thereby increase or decrease an exerciser's heart rate into one of a plurality of target heart rate zones.

In another aspect that may be combined with any of the aspects herein, each of the plurality of target heart rate zones is calculated using both an average work heart rate and a recovery heart rate of the exerciser.

In another aspect that may be combined with any of the aspects herein, the exercise system includes a heart rate monitor that monitors the exerciser's heart rate.

In another aspect that may be combined with any of the aspects herein, the heart rate monitor is worn by the exerciser.

In another aspect that may be combined with any of the aspects herein, the controller calculates the plurality of target heart rate zones.

In another aspect that may be combined with any of the aspects herein, the plurality of target heart rate zones comprise four target heart rate zones.

In another aspect that may be combined with any of the aspects herein, a lower limit of a first target heart rate zone of the plurality of target heart rate zones is calculated by subtracting 40% of the exerciser's recovery heart rate from the exerciser's average work heart rate.

In another aspect that may be combined with any of the aspects herein, an upper limit of the first target heart rate zone is calculated by subtracting 30% of the exerciser's recovery heart rate from the exerciser's average work heart rate.

In another aspect that may be combined with any of the aspects herein, a lower limit of a second target heart rate zone of the plurality of target heart rate zones is calculated by subtracting 20% of the exerciser's recovery heart rate from the exerciser's average work heart rate.

In another aspect that may be combined with any of the aspects herein, an upper limit of the second target heart rate zone is calculated by subtracting 15% of the exerciser's recovery heart rate from the exerciser's average work heart rate.

In another aspect that may be combined with any of the aspects herein, a lower limit of a third target heart rate zone of the plurality of target heart rate zones is calculated by subtracting 10% of the exerciser's recovery heart rate from the exerciser's average work heart rate.

In another aspect that may be combined with any of the aspects herein, an upper limit of the third target heart rate zone is calculated by subtracting 5% of the exerciser's recovery heart rate from the exerciser's average work heart rate.

In another aspect that may be combined with any of the aspects herein, a lower limit of a fourth target heart rate zone of the plurality of target heart rate zones is calculated by adding 5% of the exerciser's recovery heart rate to the exerciser's average work heart rate.

In another aspect that may be combined with any of the aspects herein, an upper limit of the fourth target heart rate zone is calculated by adding 10% of the exerciser's recovery heart rate to the exerciser's average work heart rate.

In another aspect that may be combined with any of the aspects herein, the heart rate monitor communicates the exerciser's heart rate to the controller.

In another aspect that may be combined with any of the aspects herein, the exerciser's average work heart rate comprises the exerciser's average heart rate during a work portion of a fitness evaluation.

In another aspect that may be combined with any of the aspects herein, the exerciser's recovery heart rate is the difference between the exerciser's heart rate at the beginning and end of a recovery portion of a fitness evaluation.

In another aspect that may be combined with any of the aspects herein, the controller generates a series of program workouts based on the plurality of target heart rate zones.

In another aspect that may be combined with any of the aspects herein, the series of program workouts may be designed to improve the exerciser's general fitness level, assist the exerciser in weight management, or improve the exerciser's performance in endurance sports.

In another aspect that may be combined with any of the aspects herein, the controller re-evaluates the exerciser's average work heart rate and recovery heart rate after a predetermined time period or after the exerciser has performed a predetermined number of workouts.

In another aspect that may be combined with any of the aspects herein, the controller recalculates the target heart rate zones based upon the exerciser's re-evaluated average work heart rate and recovery heart rate.

In another aspect that may be combined with any of the aspects herein, a method for generating and performing exercise program workouts for individual exercisers includes performing a fitness evaluation of an exerciser, including determining an average work heart rate and a recovery heart rate for the exerciser.

In another aspect that may be combined with any of the aspects herein, the method includes generating a series of program workouts based on a selected exercise program and the exerciser's average work heart rate and recovery heart rate.

In another aspect that may be combined with any of the aspects herein, the method includes running one or more program workouts from the series of program workouts.

In another aspect that may be combined with any of the aspects herein, running one or more program workouts includes adjusting an operating parameter of an exercise device to increase or decrease an intensity level of the workout and thereby increase or decrease the exerciser's heart rate into one of a plurality of target heart rate zones.

In another aspect that may be combined with any of the aspects herein, the fitness evaluation of an exerciser comprises a warm up portion, a work portion, and a recovery portion.

In another aspect that may be combined with any of the aspects herein, determining the average work heart rate of the exerciser comprises determining the average heart rate of the exerciser during the work portion of the fitness evaluation.

In another aspect that may be combined with any of the aspects herein, determining the recovery heart rate of the exerciser comprises subtracting the exerciser's heart rate at the end of the recovery portion from the exerciser's heart rate at the beginning of the recovery portion.

In another aspect that may be combined with any of the aspects herein, generating the series of program workouts comprises calculating lower and upper limits of each of the plurality of target heart rate zones.

In another aspect that may be combined with any of the aspects herein, calculating the lower and upper limits of each of the plurality of target heart rate zones comprises adding or subtracting a predetermined percentage of the exerciser's recovery heart rate from the exerciser's average work heart rate.

In another aspect that may be combined with any of the aspects herein, generating the series of program workouts comprises identifying a work-to-rest ratio associated with the selected exercise program.

In another aspect that may be combined with any of the aspects herein, the method includes performing an updated fitness evaluation of the exerciser, including determining an updated average work heart rate and an updated recovery heart rate for the exerciser.

In another aspect that may be combined with any of the aspects herein, the method includes calculating updated lower and upper limits for each of the plurality of target heart rate zones based on the exerciser's updated average work heart rate and updated recovery heart rate.

In another aspect that may be combined with any of the aspects herein, a computer program product, for implementing within an exercise system a method for enabling the generation and performance of exercise program workouts for individual exercisers, includes one or more computer readable storage media having stored thereon computer-executable instructions.

In another aspect that may be combined with any of the aspects herein, when executed by a processor, the one or more computer-executable instruction cause the exercise system to perform the method for enabling the generation and performance of exercise program workouts for individual exercisers.

In another aspect that may be combined with any of the aspects herein, the computer-executable instructions cause the exercise system to perform a fitness evaluation of an exerciser, including determining an average work heart rate and a recovery heart rate for the exerciser.

In another aspect that may be combined with any of the aspects herein, the computer-executable instructions cause the exercise system to generate a series of program workouts based on a selected exercise program and the exerciser's average work heart rate and recovery heart rate.

In another aspect that may be combined with any of the aspects herein, the computer-executable instructions cause the exercise system to run one or more program workouts from the series of program workouts.

In another aspect that may be combined with any of the aspects herein, running one or more program workouts includes adjusting an operating parameter of an exercise device to increase or decrease an intensity level of the workout and thereby increase or decrease the exerciser's heart rate into one of a plurality of target heart rate zones.

In another aspect that may be combined with any of the aspects herein, generating the series of program workouts comprises identifying a work-to-rest ratio associated with the selected exercise program.

In another aspect that may be combined with any of the aspects herein, generating the series of program workouts comprises calculating lower and upper limits of each of the plurality of target heart rate zones.

In another aspect that may be combined with any of the aspects herein, calculating the lower and upper limits of each of the plurality of target heart rate zones comprises adding or subtracting a predetermined percentage of the exerciser's recovery heart rate from the exerciser's average work heart rate.

In another aspect that may be combined with any of the aspects herein, the computer-executable instructions cause the exercise system to perform an updated fitness evaluation of the exerciser, including determining an updated average work heart rate and an updated recovery heart rate for the exerciser.

In another aspect that may be combined with any of the aspects herein, the computer-executable instructions cause the exercise system to calculate updated lower and upper limits for each of the plurality of target heart rate zones based on the exerciser's updated average work heart rate and updated recovery heart rate.

In another aspect that may be combined with any of the aspects herein, an exercise device generates exercise program workouts for use with the exercise device.

In another aspect that may be combined with any of the aspects herein, the exercise device includes a moveable element that is movable during the performance of exercise, the moveable element having one or more adjustable operating parameters.

In another aspect that may be combined with any of the aspects herein, the exercise device includes one or more processors.

In another aspect that may be combined with any of the aspects herein, the exercise device includes one or more computer storage devices having stored thereon computer-executable instructions.

In another aspect that may be combined with any of the aspects herein, the computer-executable instructions, when executed by the one or more processors, calculate an average work heart rate of an exerciser.

In another aspect that may be combined with any of the aspects herein, the computer-executable instructions, when executed by the one or more processors, calculate a recovery heart rate of the exerciser.

In another aspect that may be combined with any of the aspects herein, the computer-executable instructions, when executed by the one or more processors, calculate lower and upper limits of a plurality of target heart rate zones using both the average work heart rate and the recovery heart rate of the exerciser.

In another aspect that may be combined with any of the aspects herein, the computer-executable instructions, when executed by the one or more processors and based upon a monitored heart rate of the exerciser, cause the one or more adjustable operating parameters of the moveable element to be adjusted in order to increase or decrease an intensity level of an exercise performed by the exerciser and thereby cause the exerciser's heart rate to increase or decrease into one of the plurality of target heart rate zones.

DETAILED DESCRIPTION

Figure 1:
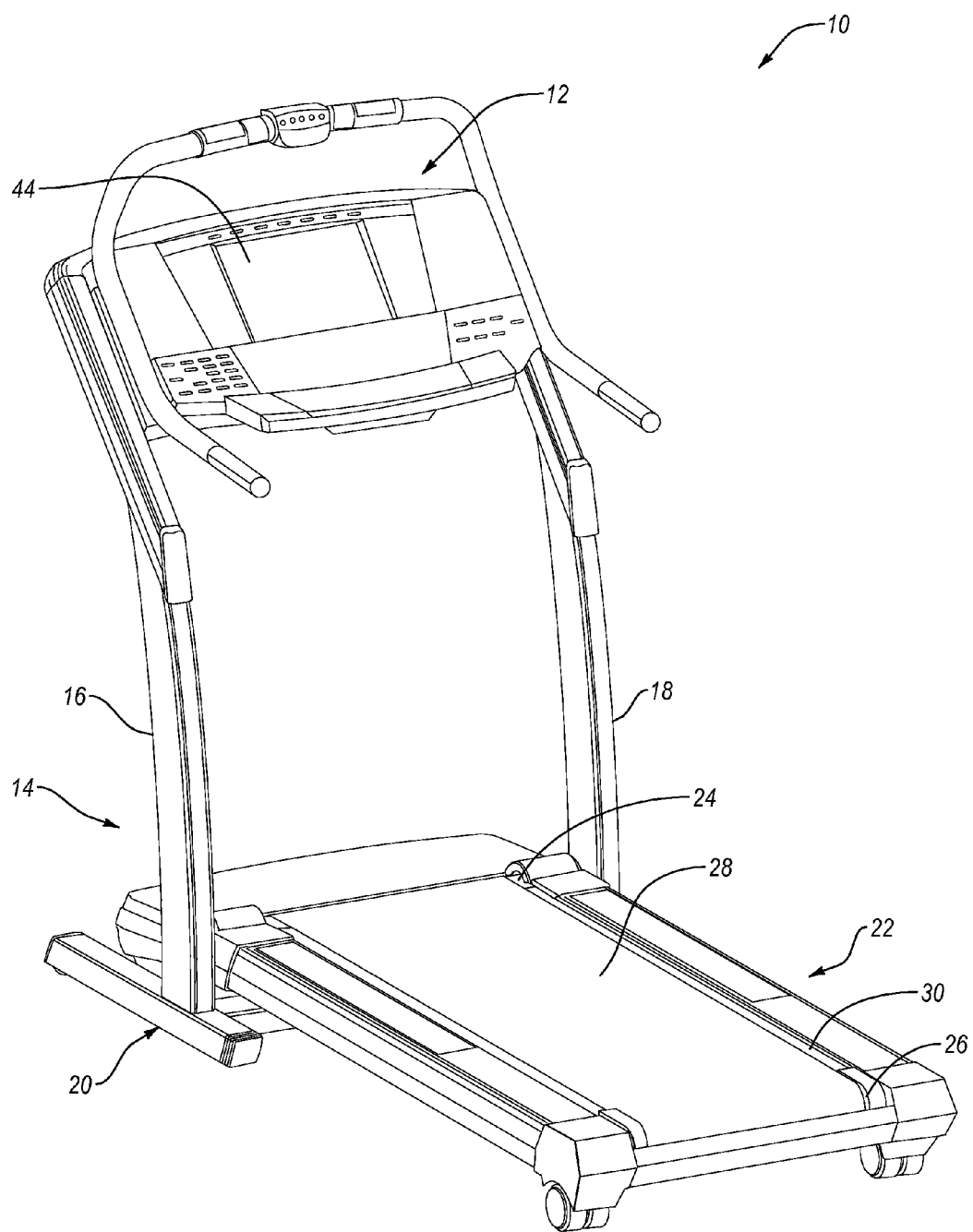
FIG. 1 illustrates a perspective view of an exercise device according to one example embodiment of the present invention.

The present disclosure is directed to systems, methods, and devices for improving cardiovascular fitness. Depicted in FIG. 1 is a representation of one illustrative exercise device 10, which may incorporate the novel features of the present invention, including various novel devices, functionalities, hardware and software modules, and the like. As shown, exercise device 10 is depicted as a treadmill and includes a console or control panel 12 supported on a generally upright support structure 14. Upright support structure 14, in this illustrated embodiment, includes two side members 16, 18 connected to a base frame 20. Side members 16, 18 and base frame 20 may have various configurations and may be fabricated from various materials so long as they are capable of supporting control panel 12.

A treadbase 22 is connected to support structure 14 and typically includes front and rear pulleys 24, 26 with a continuous belt 28 extending between and around front and rear pulleys 24, 26, respectively. Treadbase 22, front and rear pulleys 24, 26, and continuous belt 28 may be considered, individually or collectively, as movable elements that are movable during the performance of an exercise. A deck 30, commonly fabricated from wood, typically supports the upper run of belt 28 and an exercising individual positioned upon belt 28.

As is common with electric treadmills, at least one of front pulley 24 and rear pulley 26 may be mechanically connected to an electric belt drive motor 32. In the illustrated embodiment, belt drive motor 36 turns front or rear pulley 24, 26 in order to rotate belt 28. Belt drive motor 32 is electrically connected to a controller 34 that controls the operation of belt drive motor 32, and thus the speed of belt 28, in response to various inputs. The speed of belt 28 is one example of an adjustable operating parameter of exercise device 10.

Controller 34 can be incorporated within treadbase 22, control panel 12, or another portion of exercise device 10. Controller 34 may take the form of a computer, a processor, a microprocessor, a microcontroller, state machine or other similar device that includes circuitry for controlling the operation of one or more features on exercise device 10, including the operating parameter(s) of the movable element(s). As will be discussed in greater detail below, controller 34 may also perform other functions, such as evaluating an exerciser's fitness level and generating and running exercise program workouts. Controller 34 may also include one or more computer readable media or devices that have computer executable instructions stored thereon.

Figure 2:
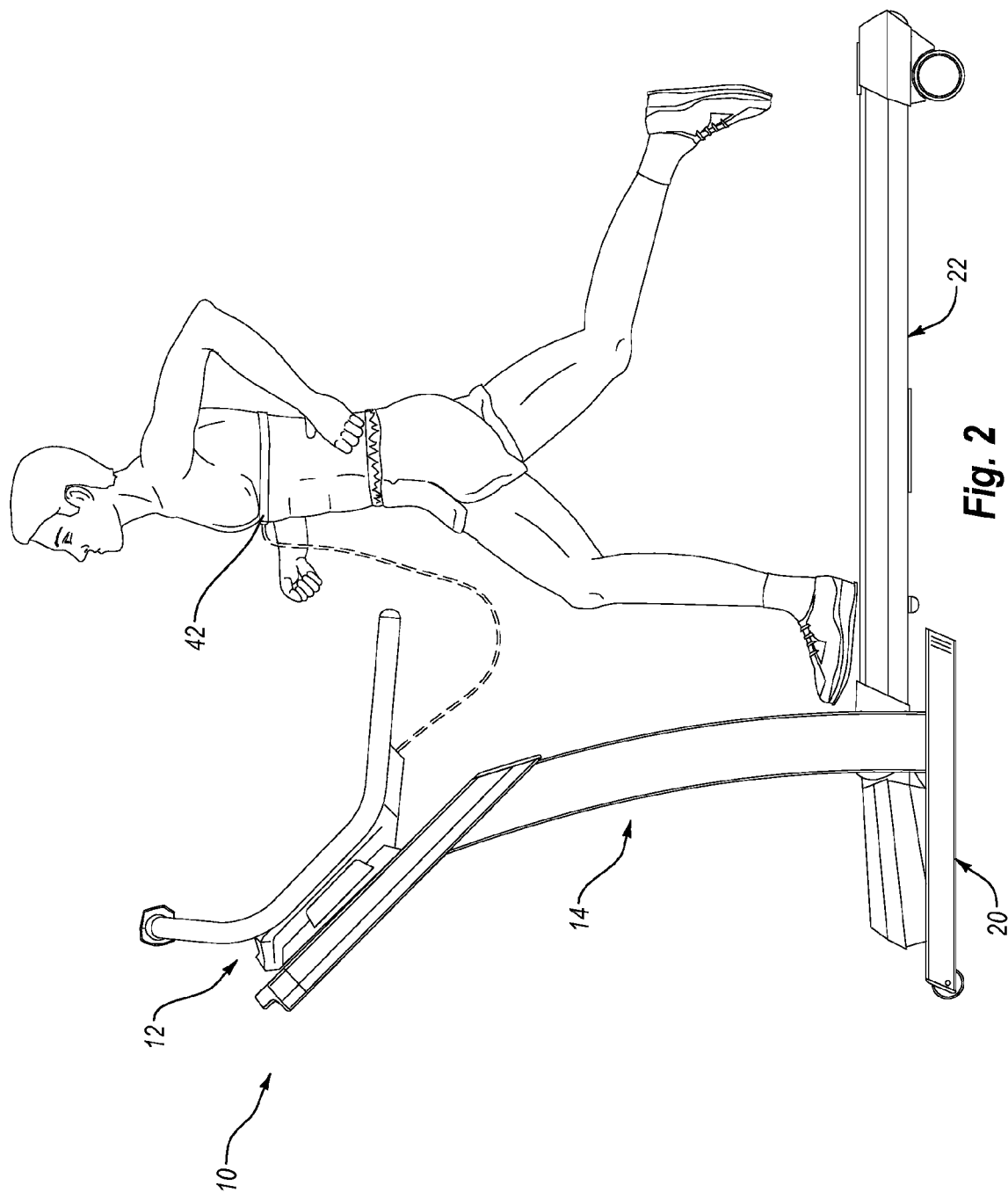
FIG. 2 is a side view of the exercise device of FIG. 1 with an exerciser exercising thereon.

In addition to the ability to control and vary the speed of belt 28, exercise device 10 may also permit the degree of incline of treadbase 22 relative to base frame 20, the floor, or other support surface upon which exercise device 10 rests, to be varied. For instance, treadbase 22 can be oriented in a neutral position, an inclined position, or a declined position. In the neutral position, treadbase 22 is generally parallel to the support surface, as shown in FIG. 2. In the inclined position, the front portion of treadbase 22 (e.g., the end of treadbase 22 adjacent to support structure 14) is vertically higher than the rear portion of treadbase 22 to enable an exerciser to simulate walking or running up a hill. Similarly, in a declined position the front portion of treadbase 22 is vertically lower than the rear portion of treadbase 22 to enable an exerciser to simulate walking or running down a hill.

The inclining and declining capabilities of treadbase 22 provide exercise device 10 with additional operating parameters that may be adjusted to vary the intensity of exercises performed on exercise device 10. The inclination and declination of treadbase 22 can be accomplished through the use of various inclination mechanisms. One example inclination mechanism includes an extension mechanism 36 connected between support structure 14 and treadbase 22. Extension mechanism 36 includes an incline motor 38 that may be controllable by controller 34 to cause an extension member 40 of extension mechanism 36 to extend or retract in order to move treadbase 22 between the declines, neutral, and inclined positions.

With continued attention to FIG. 1, attention is now directed to FIG. 2, which illustrates an exerciser exercising on exercise device 10. As can be seen in FIG. 2, the exerciser is wearing a heart rate monitor 42. Heart rate monitor 42 may detect the exerciser's heart rate or pulse (commonly referred to herein as "heart rate"). Heart rate monitor 42 may be any sensing mechanism capable of detecting the exerciser's heart rate or pulse, including electrocardiogram (EKG) monitors, pulse oximeters, photoreflectance or infrared sensor monitors, and the like. Heart rate monitor 42 may communicate the detected heart rate to exercise device 10. Such communication may be via a wired or wireless (e.g., infrared, Bluetooth, etc.) connection.

Figure 3:
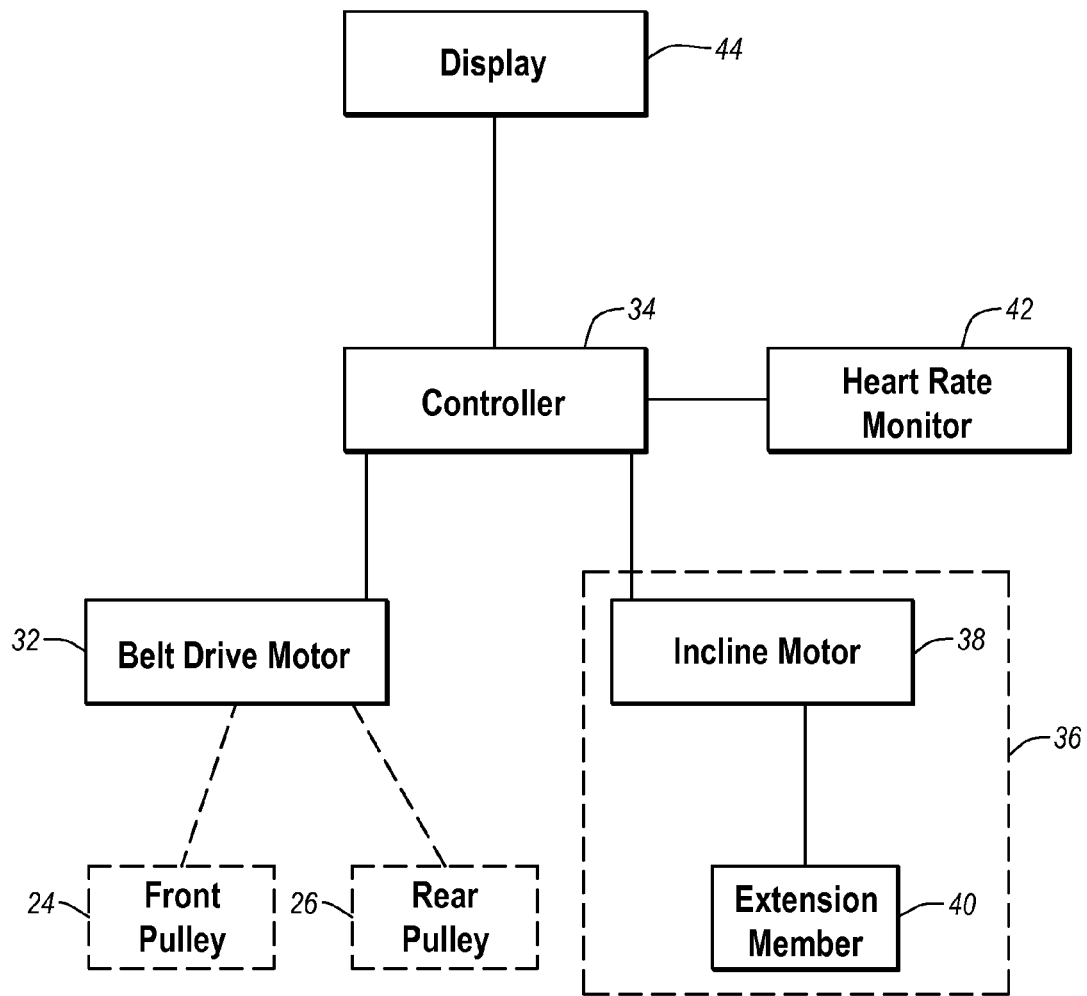
FIG. 3 is schematic representation of an exercise system according to one example embodiment of the present invention.

FIG. 3 illustrates a block diagram showing the functional relationships between heart rate monitor 42, controller 34, belt drive motor 32, incline motor 38, and a display 44 associated with control panel 12. Heart rate monitor 42 is communicatively connected to controller 34 such that heart rate monitor 42 may communicate an exerciser's heart rate to controller 34. Based on the exerciser's heart rate, controller 34 may perform various functions. For instance, as discussed in greater detail below, controller 34 may determine that the exerciser's heart rate is above, below, or within a target heart rate zone. When controller 34 determines that the exerciser's heart rate is outside the target heart rate zone, controller 34 may send one or more commands to belt drive motor 32 and/or incline motor 38 to adjust the speed of belt 28 and/or the incline of treadbase 22, thereby adjusting the intensity of the exercise performed by the exerciser. By adjusting the intensity of the exercise (increasing/decreasing the speed of belt 28 and/or the incline of treadbase 22), exercise device 10 may help bring the exerciser's heart rate into the target heart rate zone. Controller 34 may also communicate with display 44 so that display 44 may display information to the exerciser. Such information may include the target heart rate zone, the exerciser's actual heart rate, the speed of belt 28, the incline of treadbase 22, and the like.

The following portion of the description will focus primarily on the process for creating, using, and updating individually tailored exercise programs. This process includes determining the appropriate intensity levels at which an individual should exercise to achieve the highest level of success. As noted elsewhere herein, creating exercise programs specifically tailored to each individual enables more effective, efficient, and safer exercise, thereby leading to better results for each individual.

Figure 4:
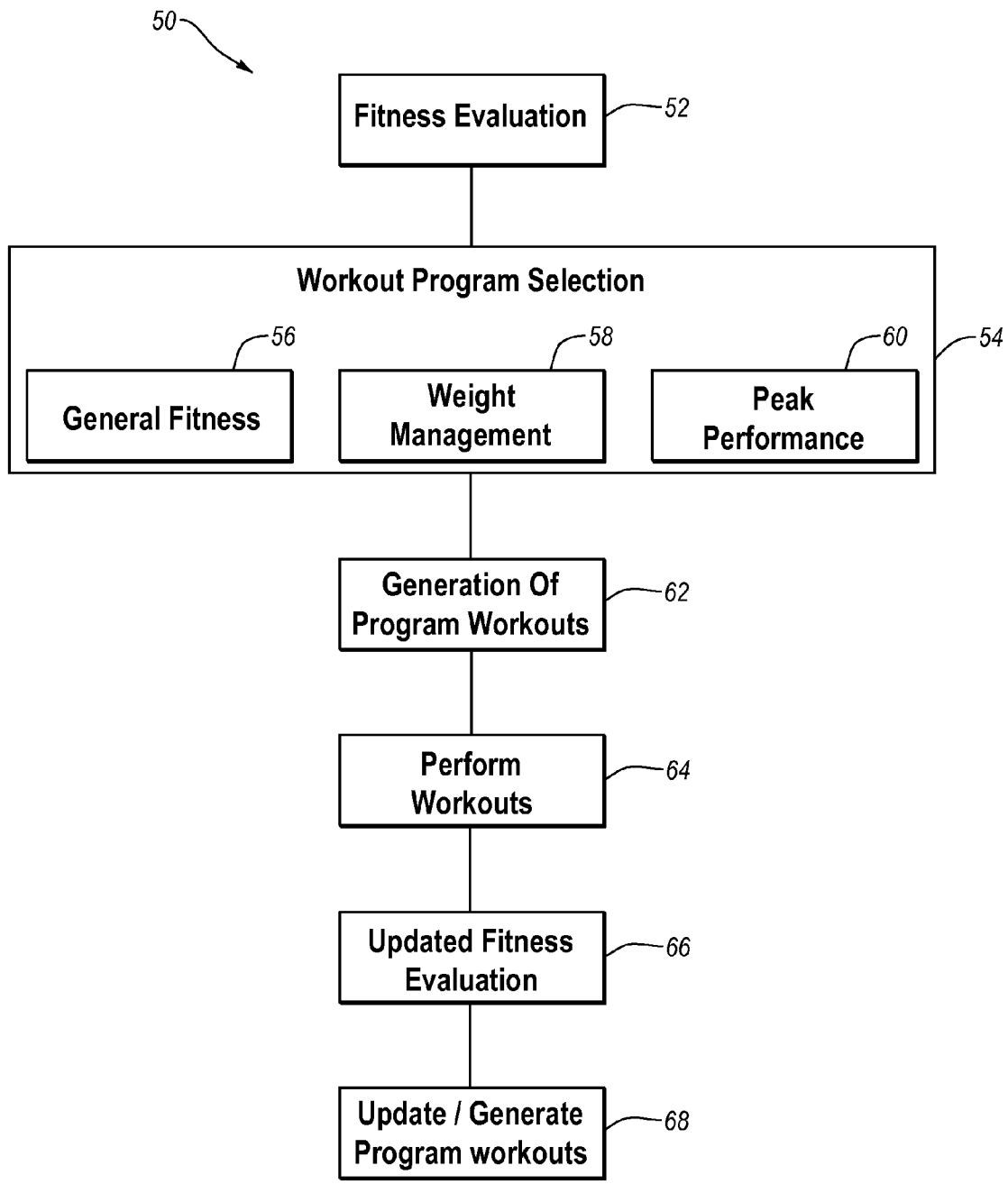
FIG. 4 is a functional block diagram of a process for creating, using, and updating individualized exercise programs.

FIG. 4 illustrates general components of a process 50 for creating, using, and updating individualized exercise programs. Following a brief overview of the components of process 50 in connection with FIG. 4, certain aspects of process 50 will be discussed in greater detail in connection with FIGS. 5-7.

Process 50 includes a fitness evaluation 52 that assesses various aspects of the exerciser's current fitness level. For instance, fitness evaluation 52 assesses the exerciser's cardiovascular fitness by monitoring certain aspects of the exerciser's heart rate under certain conditions. The assessed aspects of the exerciser's heart rate are later used to generate exercise workouts to be performed by the exerciser, as will be discussed in greater detail below.

At step 54, process 50 allows an exerciser to select the type of workout program he or she would like to perform. Display 44 may present the available workout programs to the exerciser and the exerciser may select the desired workout program using an input (e.g., button, touch-screen, etc.) on control panel 12. The types of programs available for selection by the exerciser may include, among others, a general fitness program 56, a weight management program 58, and a peak performance program 60. Each of these programs may be designed to help exercisers achieve certain fitness goals, whether those goals include losing weight, improving endurance sport performance, or simply improving one's overall fitness level.

General fitness program 56, for instance, may be designed to help exercisers increase their cardiovascular fitness, endurance, and health, even when training time is limited or exercisers want to avoid aggressive cardiovascular training. Workouts in general fitness program 56 may range from about twenty minutes to about sixty minutes and may utilize work-to-rest ratios ranging from about 1:2 to about 1:4 (e.g., for every minute of higher intensity work, there is between about 2 to about 4 minutes of rest/lower intensity work). General fitness program 56 workouts may adjust various operating parameters of exercise device 10 to vary the intensity level during each workout in order to keep the exerciser's heart rate within various target heart rate zones throughout the workout. For instance, a general fitness program 56 workout may vary one or more of the speed, incline, and resistance of exercise device 10 to adjust the intensity of a workout.

Weight management program 58 is designed to assist in proper weight control or weight loss by helping exercisers burn calories and increase fitness to sustain active lifestyles. While diet has a significant impact on weight loss, long-term weight management is highly dependent on consistent exercise and good cardiovascular fitness. Accordingly, weight management program 58 is designed to help exercisers stay consistent with their exercise habits and burn calories contributing to weight loss or the prevention of weight gain. Workouts in weight management program 58 may range from about twenty minutes to about forty-five minutes and may utilize work-to-rest ratios ranging from about 1:2 to about 1:4, primarily using a work-to-rest ratio of about 1:3. While speeds may be adjusted, weight management program 58 workouts mainly use adjustments to incline or resistance on exercise device 10 to vary the intensity levels during workouts in order to keep the exerciser's heart rate within various target heart rate zones throughout the workout. In other words, weight management program 58 workouts may keep speeds relatively low, while increasing or decreasing the incline or resistance operating parameters of exercise device 10 in order to adjust the intensity levels of the workout.

Peak performance program 60 is designed for recreational and competitive endurance athletes to help them achieve their highest fitness and optimal performance physiology. Peak performance program 60 may be a highly demanding and coordinated training routine that will push exercisers to reach the highest physiological performance. Peak performance program 60 workouts may range from about twenty minutes to about sixty minutes with work-to-rest ratios ranging from about 1:1 to about 1:3. Speed and incline/resistance may be varied to adjust the intensity levels during workouts in order to keep the exerciser's heart rate within various target heart rate zones throughout the workout. However, speeds are typically kept relatively high.

In light of the disclosure herein, it understood that the various workout programs may differ from one another in order to help an exerciser achieve his or her specific goals. Thus, depending on the fitness goals, the workout programs may differ in their length, work-to-rest ratios, and intensity levels/target heart rate zones. For instance, peak performance program 60 workouts may be longer, with more time spent in higher intensity target heart rate zones, and may use higher speeds than the other workout programs. In contrast, weight management program 58 workouts may use higher inclines or greater resistance to move the exerciser's heart rate between the target heart rate zones since higher inclines and greater resistances result in greater calorie burn.

With fitness evaluation 52 completed and the type of workout program (e.g., 56, 58, 60) selected, program workouts are generated at step 62. Generation of program workouts 62 creates a six month progression or series of workouts for the exerciser to perform based on the type of exercise program the exerciser selected and the exerciser's current fitness level as determined by fitness evaluation 52. The series of workouts may include 20 workouts per month. Training stress may be altered from workout to workout, week to week, and month to month. At the end of the six month sequence, process 50 can begin again. While each program may provide enough workouts for six months of exercise, exercisers that exercise more frequently may complete the series of workouts in less than six months. Such exercisers can simply begin process 50 again whenever they complete the previous series of workouts.

Once the workouts have been generated, the exerciser then performs one or more of the series of generated workouts (e.g., step 64). As discussed elsewhere herein, performing the workouts includes exercising on exercise device 10 at various intensity levels so that the exerciser's heart rate moves between various target heart rate zones.

After completing a certain number of generated workouts (e.g., 20 workouts) or after a given time period (e.g., one month from the time fitness evaluation 52 is completed), an updated fitness evaluation 66 is performed to reassess the exerciser's fitness level. Updated fitness evaluation 66 can be similar or identical to fitness evaluation 52. Specifically, updated fitness evaluation 66 may assess the exerciser's cardiovascular fitness by monitoring the same aspects of the exerciser's heart rate under the same conditions as fitness evaluation 52. Based on the results of updated fitness evaluation 66, the previously generated workouts are updated or new workouts are generated for the exerciser to perform, as indicated at 68.

Figure 5:
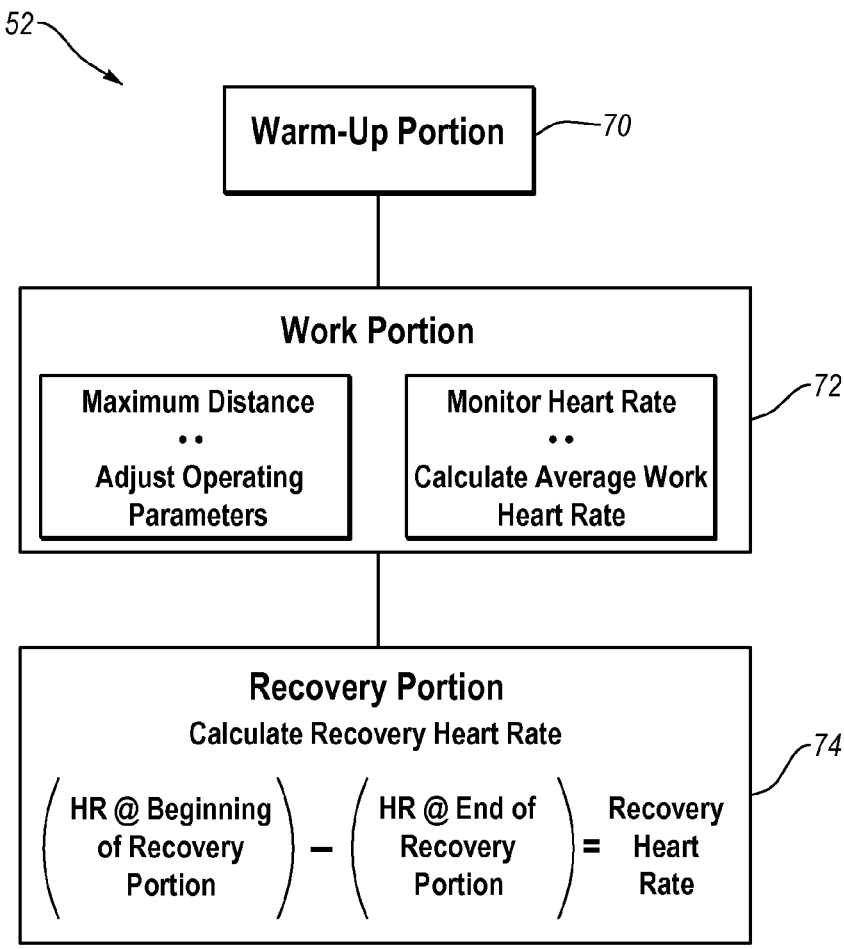
FIG. 5 is a functional block diagram of a process for performing a fitness evaluation of an exerciser.

Attention is now directed to FIG. 5, which illustrates a functional block diagram depicting various exemplary aspects of fitness evaluation 52. The following description of fitness evaluation 52 may also be equally applicable to updated fitness evaluation 66. In other words, updated fitness evaluation 66 may include the same or similar components and features as fitness evaluation 52.

According to the present embodiment, fitness evaluation 52 includes three primary components, namely, a warm-up portion 70, a work portion 72, and a recovery portion 74, which an exerciser performs on exercise device 10. Fitness evaluation 52 is designed to assess certain aspects of the exerciser's cardiovascular fitness. Accordingly, during fitness evaluation 52, the exerciser wears heart rate monitor 42 so that the exerciser's heart rate may be monitored, as shown in FIG. 2.

Fitness evaluation 52 begins with warm-up portion 70 during which the exerciser progressively works into an exercise mode, such as by progressively increasing the speed of belt 28. Warm-up portion 70 lasts for a relatively short time period, such as about three minutes.

At the end of warm-up portion 70, the exerciser begins work portion 72. During work portion 72, the exerciser's goal is to go as far as possible or exercise at the highest sustainable rate. For instance, an exerciser that is in excellent physical shape may be able to run three miles on exercise device 10 during work portion 72, while an exerciser that is in poor shape may be able to walk on exercise device 10 less than one mile during work portion 72. Accordingly, the exerciser can adjust the operating parameters of exercise device 10, such as the speed of belt 28, as desired to enable the exerciser to go as far as he or she can or at his or her highest sustainable rate during work portion 72. The duration of work portion 72 may be adjusted, but according to some embodiments work portion 72 lasts for about twenty minutes.

During work portion 72, heart rate monitor 42 monitors the exerciser's heart rate. At the end of work portion 72, the exerciser's average heart rate during work portion 72 (also referred to as the exerciser's average work heart rate or AWHR) is calculated. Heart rate monitor 42 may calculate the exerciser's average work heart rate and then communicate the exerciser's average work heart rate to controller 34. Alternatively, heart rate monitor 42 may continuously or intermittently monitor the exerciser's heart rate during work portion 72 and communicate this data to controller 34, which may calculate the exerciser's average work heart rate.

Upon completion of work portion 72, the exerciser finishes fitness evaluation 52 with recovery portion 74. During recovery portion 74, the exerciser slows to a very slow pace, such as less than about two miles per hour, for a period of recovery. In one embodiment, recovery portion 74 lasts for about two minutes. Upon completion of recovery portion 74, the exerciser's recovery heart rate or RHR is calculated. The exerciser's recovery heart rate is the difference between the exerciser's heart rate at the beginning of recovery portion 74 and at the end of recovery portion 74. For instance, if the exerciser's heart rate drops from 180 beats per minute (bpm) at the beginning of recovery portion 74 to 110 bpm at the end of recovery portion 74, the exerciser's recovery heart rate is 70 bpm (e.g., 180−110=70).

Fitness evaluation 52 provides at least two key fitness indicators, namely, the total distance traveled during work portion 72 and the recovery heart rate. The following Table 1 can be used to help evaluate an exerciser's fitness level with either of these indicators. For instance, if the exerciser is able to run more than 3.4 miles during work portion 72 or if his or her recovery heart rate is greater than 90 bpm (e.g., heart rate drops by more than 90 bpm during recovery portion 74), the exerciser is likely in superior physical condition. In contrast, if the exerciser is able to go less than one mile during work portion 72 or if his or her recovery heart rate is less than 45 bpm (e.g., heart rate drops by less than 45 bpm during recovery portion 74), the exerciser is likely in poor physical condition. In addition to providing a general evaluation of an exerciser's fitness level, and as discussed below, the exerciser's recovery heart rate is also used in generating the workouts to be performed.

TABLE 1

| Rating | Distance (miles) | Recovery Heart Rate |
|---|---|---|
| Poor | 0-1.0 | 0-45 |
| Average | 1.1-1.9 | 46-60 |
| Good | 2.0-2.8 | 61-75 |
| Excellent | 2.9-3.4 | 76-90 |
| Superior | >3.4 | >90 |

Figure 6:
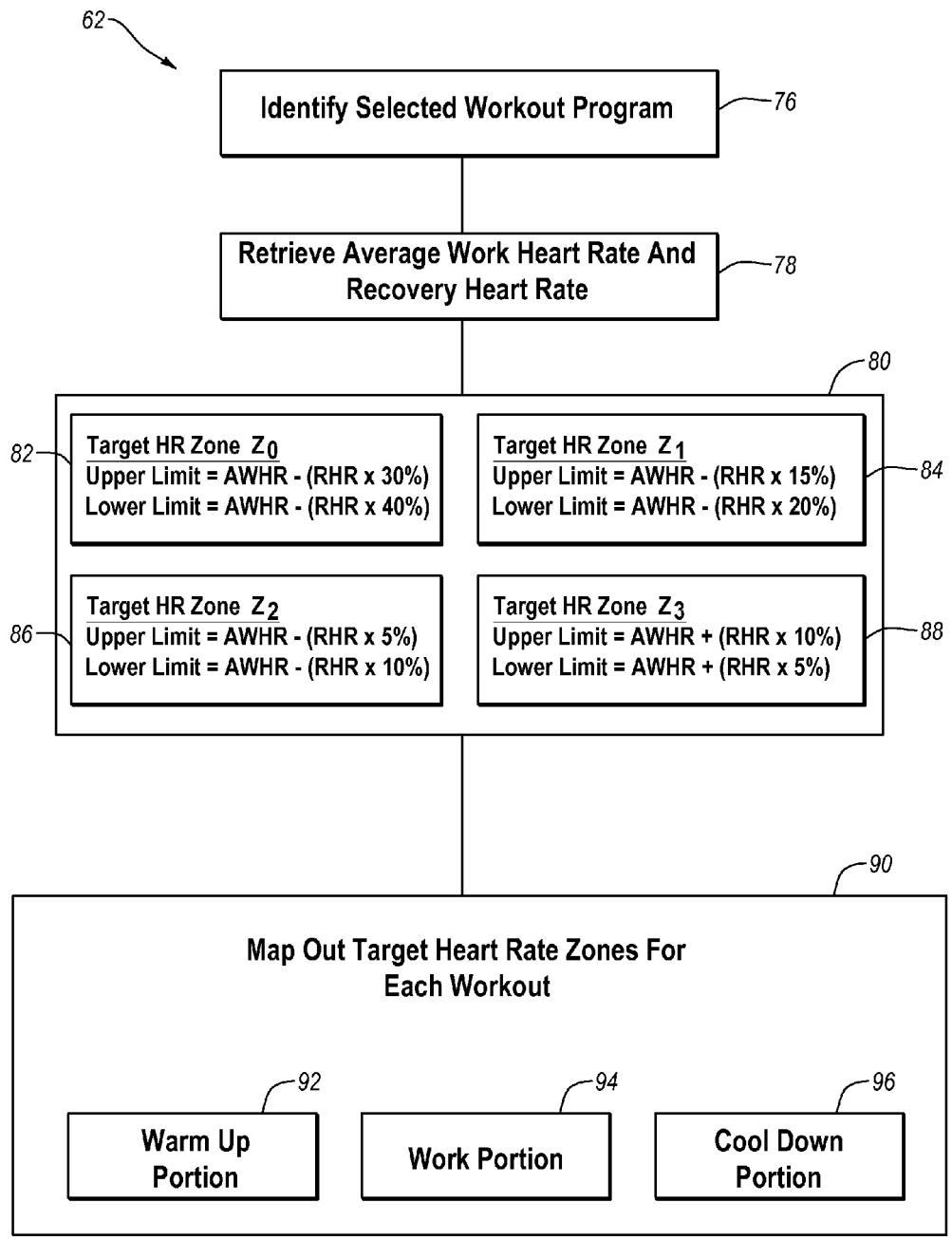
FIG. 6 is a functional block diagram of a process for generating exercise program workouts.

As noted above, once fitness evaluation 52 is completed and the exerciser has selected the type of exercise program to be performed, the series of workout are generated (FIG. 4, step 62). FIG. 6 illustrates a flow diagram of various example aspects of the generation of program workouts 62. In the illustrated embodiment, generation of program workouts 62 includes identifying the workout program (e.g., general fitness program 56, weight management program 58, peak performance 60) selected by the exerciser as well as retrieving the exerciser's heart rate information obtained during fitness evaluation 52, as indicated in FIG. 6 at reference numbers 76 and 78, respectively.

The exerciser's heart rate information obtained during fitness evaluation 52 is used to calculate target heart rate zones for the series of workouts, as indicated at reference number 80. As noted herein, other heart rate based fitness systems use generic heart rates or heart rate zones, such as age-predictive or other non-individualized heart rates/zones, when establishing a training program. In contrast, embodiments of the present invention use data specific to each exerciser when generating workouts. As a result, the workouts generated according to the present invention are custom tailored to each exerciser.

According to the present embodiment, four target heart rate zones, $Z_0$, $Z_1$, $Z_2$, $Z_3$, are used in generating the series of workouts. As shown in FIG. 6 at reference numbers 82, 84, 86, 88, target heart rate zones, $Z_0$, $Z_1$, $Z_2$, $Z_3$ are calculated using unique combinations of each exerciser's average work heart rate (AWHR) and recovery heart rate (RHR). For instance, the upper and lower limits of each target heart rate zone may be calculated by subtracting or adding a certain percentage of the exerciser's recovery heart rate from the exerciser's average work heart rate.

For instance, according to the present embodiment, an upper limit of target heart rate zone $Z_0$ may be calculated by subtracting 30% of the exerciser's recovery heart rate from the exerciser's average work heart rate. A lower limit of target heart rate zone $Z_0$ may be calculated by subtracting 40% of the exerciser's recovery heart rate from the exerciser's average work heart rate. The upper and lower limits of target heart rate zone $Z_1$ may be calculated by subtracting 15% and 20% of the exerciser's recovery heart rate, respectively, from the exerciser's average work heart rate. Similarly, the upper and lower limits of target heart rate zone $Z_2$ may be calculated by subtracting 5% and 10% of the exerciser's recovery heart rate, respectively, from the exerciser's average work heart rate.

In calculating the upper and lower limits for target heart rate zone $Z_3$, certain percentages of the exerciser's recovery heart rate are added to the exerciser's average work heart rate rather than being subtracted therefrom. According to the present embodiment, for instance, 10% of the exerciser's recovery heart rate is added to the exerciser's average work heart rate to determine the upper limit for target heart rate zone $Z_3$. Similarly, 5% of the exerciser's recovery heart rate is added to the exerciser's average work heart rate to determine the lower limit for target heart rate zone $Z_3$.

By way of example, the upper and lower limits of target heart rate zones $Z_0$, $Z_1$, $Z_2$, $Z_3$ for an exerciser that has an average work heart rate of 180 bpm and a recovery heart rate of 70 bpm are calculated as follows:
  Target Heart Rate Zone $Z_0$
    Lower Limit: 180−(70·40%)=152
    Upper Limit: 180−(70·30%)=159
  Target Heart Rate Zone $Z_1$
    Lower Limit: 180−(70·20%)=166
    Upper Limit: 180−(70·15%)=170
  Target Heart Rate Zone $Z_2$
    Lower Limit: 180−(70·10%)=173
    Upper Limit: 180−(70·5%)=177
  Target Heart Rate Zone $Z_3$
    Lower Limit: 180+(70·5%)=184
    Upper Limit: 180+(70·10%)=187

As indicated in FIG. 6 at reference number 90, generation of program workouts 62 also includes mapping out the target heart rate zones for each of the series of program workouts. In discussing the mapping out of target heart rate zones for each workout, reference will be made to Appendices A, B, and C, which are attached hereto. Appendices A, B, and C include examples of workouts generated via generation of program workouts 62. For instance, Appendix A includes tables of example workouts for general fitness program 56. Similarly, Appendix B includes tables of example workouts for weight management program 58 and Appendix C includes tables of example workouts for peak performance program 60. Each Appendix includes six months of workouts, with twenty workouts for each month.

Each workout has the exerciser exercise at multiple intensity levels to vary the exerciser's heart rate as he or she exercises. For instance, each workout may include a warm up portion 92, a work portion 94, and a cool down portion 96. Warm up portion 92 may begin by having the exerciser exercise at a relatively low intensity level that will begin to raise the exerciser's heart rate. By way of example, each of the workouts in Appendices A, B, and C includes a five minute warm up portion. These warm up portions begin by having the exerciser exercise for two minutes at an intensity that will raise the exerciser's heart rate into target heart rate zone $Z_0$. The warm up portions then have the exerciser exercise for three minutes at an intensity that will raise the exerciser's heart rate into target heart rate zone $Z_1$. Thus, according to some embodiments, warm up portion 92 utilizes target heart rate zones $Z_0$ and $Z_1$.

After warm up portion 92, each workout includes a work portion 94 that has the exerciser exercise at higher intensity levels, which are designed to help the exerciser achieve his or her fitness goals. According to the present embodiment, work portion 92 utilizes target heart rate zones $Z_2$ and $Z_3$. For instance, the work portion of the first workout from month one of general fitness program 56 shown in Appendix A alternates between target heart rate zones $Z_2$ and $Z_3$. According to the sample workout, target heart rate zones $Z_2$ and $Z_3$ are alternated at a work-to-rest ratio of 1:4. That is, for every minute of exercise in target heart rate zone $Z_3$, the workout includes four minutes of exercise in target heart rate zone $Z_3$.

When included, cool down portion 96 may reduce the intensity level of the exercise to allow the exerciser to gradually reduce his or her heart rate and recover from work portion 94. For instance, cool down portion 96 may include two minutes of exercise at target heart rate zone $Z_1$ followed by one minute of exercise at target heart rate zone $Z_0$.

Upon review of the workouts in Appendices A, B, and C, it is noted that the characteristics of the workouts may vary from workout to workout and from month to month. For instance, the work-to-rest ratio from workout to workout may vary. As noted above, for instance, the work-to-rest ratios for the general fitness program 56 workouts may vary from 1:1 to 1:4. The work-to-rest ratio for each workout is indicated at the bottom of each table. In addition to varying the work-to-rest ratio, the length of the workouts can be varied. As seen in the sample workouts, the length of the workouts can be varied by adding or removing one or more work-to-rest cycles from work portion 94.

By varying the work-to-rest ratio and/or the length of the workouts, the demand of the workouts may be varied. The demand of each workout may be a representation of the work required to perform the workout. According to the present embodiment, the demand for each workout may be calculated by adding the numerical values of the target heart rate zones (e.g., $Z_0=0$, $Z_1=1$, $Z_2=2$, $Z_3=3$) in the workout. For instance, the first workout from month one of general fitness program 56 shown in Appendix A includes two minutes in zone $Z_0$, three minutes in zone $Z_1$, twelve minutes in zone $Z_2$, and two minutes in zone $Z_3$. Accordingly, the demand for this workout may be calculated as:

$$(2 \cdot 0)+(3 \cdot 1)+(12 \cdot 2)+(2 \cdot 3)=33$$

As seen in the sample workouts, the workout demands may change from day to day and month to month. Varying and progressively increasing the workout demands results in an increase in the exerciser's fitness level as well as compensates for the exerciser's improved fitness level. In other words, varying and increasing the workout demands helps to improve the exerciser's fitness level and continues to push the exerciser to ever higher fitness levels.

Figure 7:
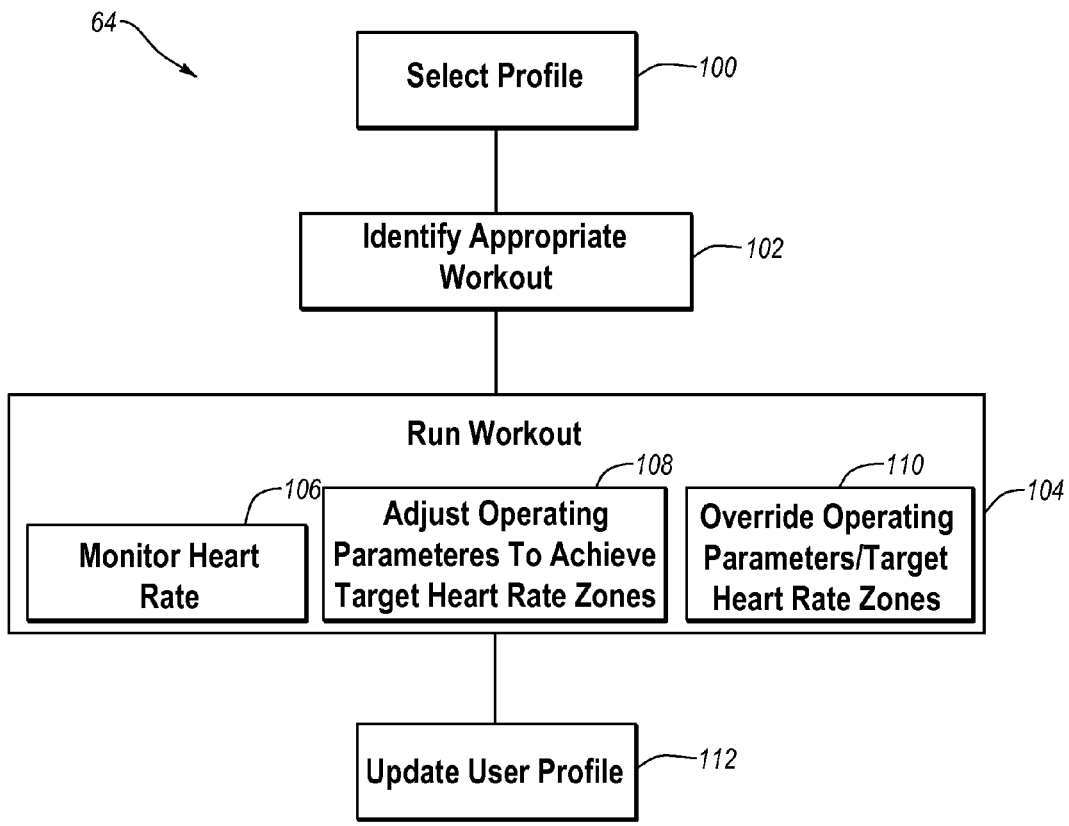
FIG. 7 is a functional block diagram of a process for performing exercise program workouts.

As indicated at reference number 64 in FIG. 4, with the series of program workouts generated, an exerciser may begin to perform the workouts by exercising on exercise device 10. FIG. 7 illustrates a flow diagram of various example aspects of performing the workouts. Exercise device 10 may allow an exerciser to create a profile so that exercise device 10 may track the exerciser's progress through the series of workouts, such as which exercise workouts the user has already completed.

As indicated at 96, each time the exerciser exercises, the exerciser may select his or her profile on exercise device 10. Exercise device 10 may then identify the appropriate workout for the exerciser to perform, as indicated at reference number 102. For instance, when the exerciser first begins an exercise program, exercise device 10 may identify that the exerciser should perform the first workout in month one of the series of workouts. On the other hand, since exercise device 10 may track the exerciser's progress through the series of workouts, exercise device 10 may know that the exerciser has already performed, for example, the first five workouts in month one. In such a situation, exercise device 10 may identify workout six from month one for the exerciser to perform.

Upon identification of the appropriate workout, exercise device 10 may run the identified workout, as indicated at reference number 104. As part of running a workout, exercise device 10, by way of or in combination with heart rate monitor 42, monitors the exerciser's heart rate, as indicated at reference number 106.

In addition to monitoring the exerciser's heart rate, exercise device 10 also adjusts the operating parameters of the movable elements of exercise device 10, as indicated at reference number 108. Exercise device 10 adjusts the operating parameters in order to vary the intensity level of the workout, and thereby move the exerciser's heart rate into the appropriate target heart rate zone. In other words, if an exerciser's heart rate should be in a certain target heart rate zone at a particular time in the workout, exercise device 10 may adjust the operating parameters of the movable elements in order to increase or decrease the exerciser's heart rate into the certain target heart rate zone. Thus, for example, when moving an exerciser between target heart rate zones $Z_2$ and $Z_3$, exercise device 10 may increase the speed of belt 28, the incline of treadbase 22, or a combination thereof, to increase the exerciser's heart rate from the target heart rate zone $Z_2$ level to the target heart rate zone $Z_3$ level. Thus, exercise device 10 may vary the operating parameters as needed in order to adjust the intensity levels of the workout so that the exerciser's heart rate is moved into and/or remains in the specified target heart rate zone.

At any point during the workout, the exerciser may override the operating parameters of exercise device 10, as indicated at reference number 110. For instance, if an exerciser becomes overly fatigued during a workout, the exerciser can cause exercise device 10 to adjust the operating parameters to reduce the level of intensity of the workout. The exerciser can, for example, activate one or more inputs on control panel 12 that cause the speed of belt 28 or the incline of treadbase 22 to decrease.

At the completion of each workout, the exerciser's profile may be updated, as indicated at reference number 112. Updating the exerciser's profile may include recording the completion of the workout, the date the workout was performed, and other data relating to the exerciser's performance of the workout.

Periodically an updated fitness evaluation 66 is performed to reassess the exerciser's fitness level, as shown in FIG. 4. As indicated above, updated fitness evaluation 66 may be similar or identical to fitness evaluation 52. Accordingly, updated fitness evaluation 66 may assess the exerciser's average work heart rate and recovery heart rate, as well as the exerciser's fitness level as indicated by the distance the exerciser is able to go during the work portion of the fitness evaluation.

According to the present embodiment, updated fitness evaluation 66 is initially performed after the earlier of the exerciser's completion of the first month's workouts (e.g., first twenty workouts) or one month after fitness evaluation 52. Subsequently, updated fitness evaluation 66 is performed after the earlier of the exerciser's completion of the most recent month's workouts or one month after the last performance of updated fitness evaluation 66. In other words, an updated fitness evaluation 66 may be performed at least monthly or sooner if the exerciser completes all of the workouts from the previous month early.

Accordingly, prior to or simultaneously with identifying the appropriate workout for the exerciser to perform, as indicated at reference number 102 in FIG. 7, exercise device 10 may determine whether the exerciser has completed all of the workouts for the previous month or if it has been at least one month since fitness evaluation 52 or updated fitness evaluation 66 was performed. If the exerciser has completed all of the workouts from the previous month or if it has been at least one month since the performance of fitness evaluation 52 or updated fitness evaluation 66, exercise device 10 may indicate to the exerciser that an updated fitness evaluation 66 needs to be performed before advancing through the series of workouts.

Periodically performing an updated fitness evaluation 66 allows the exerciser's fitness level to be monitored and the program workouts tailored to help the exerciser achieve his or her fitness goals in a safe manner. For instance, regularly reassessing the exerciser's fitness level enables the program workouts to be tailored to the exerciser's current fitness level. As a result, the intensity levels of the program workouts may be set at levels that sufficiently push the exerciser to higher fitness level while avoiding intensity levels that are unsafe or beyond the exerciser's current abilities.

The information obtained during updated fitness evaluation 66 (e.g., the exerciser's new average work heart rate and new recovery heart rate) is used to update the previously generated workout programs or to generate new workout programs, as indicated at reference number 68 in FIG. 4. Updating or generating program workouts at step 68 may include recalculating the exerciser's target heart rate zones. By way of example, if after a month of workouts, an exerciser's average work heart rate has increased from 180 bpm to 190 bpm and the exerciser's recovery heart rate has increased from 70 bpm to 78 bpm, then the exerciser's target heart rate zones would likewise increase. The following Table 2 provides a comparison between the example exerciser's old target heart rate zones and the example exerciser's new target heart rate zones, which are calculated in the same manner as discussed above (e.g., adding or subtracting certain percentages of the recovery heart rate from the average work heart rate).

TABLE 2

| Zone | Old Target Heart Rate Zones | | New Target Heart Rate Zones | |
|---|---|---|---|---|
| | Lower Limit | Upper Limit | Lower Limit | Upper Limit |
| $Z_0$ | 152 | 159 | 159 | 167 |
| $Z_1$ | 166 | 170 | 174 | 178 |
| $Z_2$ | 173 | 177 | 182 | 186 |
| $Z_3$ | 184 | 187 | 194 | 198 |

As can be seen in Table 2, as the exerciser's cardiovascular fitness improves (as indicated by a higher average work heart rate and higher recovery heart rate), the target heart rate zones increase. In addition to the improvement in the exerciser's cardiovascular fitness resulting from the exerciser's progression through the series of workouts, the exerciser's cardiovascular fitness improvement may also result from activities not performed on exercise device 10. For instance, such activities as going for a jog around town, riding a bike, playing tennis, and the like, may all contribute to improved cardiovascular fitness. When reassessing the exerciser's cardiovascular fitness level, updated fitness evaluation 66 will account for all of the activities the exerciser has performed, not just the performance of the program workouts.

With the newly calculated target heart rate zones, the exerciser may continue to perform the series of program workouts. If the exerciser's cardiovascular fitness level has improved, the target heart rate zones for the next month of workouts will be higher than the previous months, as indicated in Table 2. As a result, exercise device 10 will increase the intensity level of the workouts (via changes in the operating parameters) in order move the exerciser's heart rate into the higher target heart rate zones. Alternatively, if the exerciser's cardiovascular fitness level has decreased, as a result of not performing enough exercise in the previous month, exercise device 10 will decrease the intensity level of the workouts (via changes in the operating parameters) in order move the exerciser's heart rate into the lower target heart rate zones.

Because the target heart rate zones are altered based on the exerciser's current cardiovascular fitness level, the exerciser may go through process 50 repeatedly. Each time the exerciser goes through process 50, the program workouts will be tailored to the exerciser's fitness level, thereby continuing to challenge the exerciser and improve his or her cardiovascular fitness level. In other words, process 50 is a self updating process that provides program workouts tailored to individual exercisers so that the intensity levels of the workouts are appropriate for the exerciser regardless of how many times the exerciser has gone through process 50.

Many of the aspects described above may be automated using a computing device. For instance, exercise device 10 may include a special purpose or general-purpose computing device, including various computer hardware. Controller 34 may be one example of such a computing device. Embodiments of the present invention may also include computer-readable media (devices) for carrying or having computer-executable instructions or data structures stored thereon. Such computer-readable media can be any available media that can be accessed by a general purpose or special purpose computing device. By way of example only, such computer-readable media can include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to carry or store desired program code means in the form of computer-executable instructions or data structures which can be accessed by a general purpose or special purpose computing device.

As used herein, computer-executable instructions may include, for example, instructions and data which, when executed, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

INDUSTRIAL APPLICABILITY

In general, embodiments of the present disclosure relate to exercise systems, devices, and methods that enable an exerciser to exercise more effectively and efficiently. The systems, devices, and methods of the present disclosure evaluate an exerciser's cardiovascular fitness and create exercise programs that are custom tailored to each individual exerciser, rather than employing a generic fitness evaluation that likely will not accurately reflect the exerciser's actual fitness level.

For instance, in one embodiment, an exerciser's cardiovascular fitness level is evaluated by monitoring the exerciser's heart rate during an evaluation exercise session. After a short warm-up period (e.g., about two or three minutes), the exerciser exercises for a given work period, such as twenty minutes, and the exerciser's average heart rate is calculated for the work period. At the end of the work period, the exerciser continues to exercise at a very low rate during a cool down period. At the end of the cool down period, the exerciser's recovery heart rate is calculated. The exerciser's recovery heart rate is calculated by determining the difference between the exerciser's heart rate at the beginning of the cool down and at the end of the cool down period.

The exerciser's average work period heart rate and recovery heart rate are indicators of the exerciser's cardiovascular fitness level. Accordingly, the systems, devices, and methods of the present disclosure use the exerciser's average work period heart rate and recovery heart rate to create customized workouts that are tailored for the specific exerciser at the exerciser's current cardiovascular fitness level. More specifically, the exerciser's average work heart rate and recovery heart rate are both used to determine the proper exercise intensity at which the exerciser should exercise.

Embodiments of the invention may provide a series of workouts for the exerciser to perform. The demand required by the series of workouts may vary from workout to workout, week to week, and month to month. Additionally, the series of workouts may include enough workouts for a given period of time, such as six months. At periodic points during the series of workouts, the exerciser's cardiovascular fitness level may be reevaluated and the workouts adjusted so that the intensity levels of the workouts are commensurate with the exerciser's current fitness level.

Each workout requires the exerciser to exercise at various intensity levels so that the exerciser's heart rate moves between different predetermined target heart rate zones. The target heart rate zones are calculated from data relating to the exerciser's cardiovascular fitness level. Specifically, the target heart rate zones are calculated using both the exerciser's average work heart rate and the exerciser's recovery heart rate.

While embodiments of the invention have been described in the context of a motorized treadmill, it is understood that the invention is not limited to any particular type of exercise device. Accordingly, the term "exercise device" shall refer broadly to any type of device that takes the form of an exercise machine, including, but not limited to, treadmills, exercise cycles, Nordic style ski exercise devices, rowers, steppers, hikers, climbers, and elliptical or striding exercise devices. These various types of exercise devices may include adjustable operating parameters similar to those described above (e.g., speed, incline, etc.). Additionally, these exercise devices may also have adjustable operating parameters such as resistance to the movement of a movable element (e.g., belt, pedal, link arm, etc.). Accordingly, these various operating parameters may be adjusted in order to change the intensity level of a workout as described herein.

The effectiveness of the disclosed cardiovascular training system was compared to that of two other cardiovascular training systems. In comparing the three systems, a ten week trial was conducted with ninety adults, both men and women, between the ages of 18-45. The participants represented a range of fitness abilities from untrained to competitive endurance athletes. The participants were divided into three groups. In all, each group was a fairly representative sample of the surrounding community and not substantially different from the other groups.

During the trial, the first group used the presently disclosed cardiovascular training system, the second group used a metabolic based training system based on anaerobic threshold, and the third group used an age-predicted heart rate training system. Each group performed exercises according to the system to which they were assigned, training 3-5 days per week, 20-60 minutes per day for 10 weeks. All of the participants were required to adhere to the exercise programs exactly as outlined and to follow an individually developed nutrition programmed. Thus, the only significant difference between the three groups was the exercise system being employed.

The training that each group performed over the ten weeks was dependant on the training system to which they were assigned. The first group performed a combination of the three programs described above (e.g., general fitness, weight management, and peak performance). The age-predicted group followed recommendations from the American College of Sports Medicine (ACSM) for training with heart rate zones calculated at 60-85% of an age-predicted heart rate. The metabolic training group was tested on an iMett metabolic cart and then followed training zones based on anaerobic threshold.

Before and after the ten week training programs, fitness testing was conducted to examine the difference in fitness development. Metabolic testing to examine a variety of different fitness variables was conducted and statistical evaluation was conducted to compare the different training programs. The tests included:

Two-minute recovery heart rate—a measure of how fast heart rate drops after stopping a fitness test. The faster the heart rate drops, the better the fitness.

Ventilatory threshold—a measure of when the body changes predominantly from an aerobic energy source to an anaerobic energy source. The higher the exercise intensity when this occurs, the better the fitness. Heart rate, power, and oxygen consumption were measured at ventilatory threshold to allow for multiple measures surrounding this variable.

Maximum aerobic power—a measure of how much power the exerciser can produce at peak capacity The data collected during the trial study demonstrated that the cardiovascular training system described herein resulted in greater weight loss and improvements in fitness than the other two programs. For instance, the presently disclosed system resulted in 54% greater weight loss than the metabolic training and 42% more than the age-predicted training. The presently disclosed system also resulted in 124% greater improvement in recovery heart rate than the metabolic training and 115% greater improvement than the age-predicted training. Additionally, the presently disclosed system lead to a 159% greater improvement in heart rate at ventilatory threshold compared to the metabolic training and 162% greater improvement than the age-predicted training. Further, the presently disclosed system also leads to an 82% greater change in maximum aerobic power as compared to the metabolic training and 83% more than the age-predicted training. Still further, the presently disclosed system lead to a 99% greater improvement in oxygen consumption at ventilatory threshold than the metabolic training and 112% more than the age-predicted training. Moreover, the presently disclosed system resulted in a 118% improvement in power at ventilatory threshold as compared to the metabolic training and 183% greater than the age-predicted training.

What is claimed is:

1. An exercise system, comprising:
    a movable element that is movable in the performance of an exercise, the movable element having at least one selectively adjustable operating parameter; and
    a controller that adjusts the at least one selectively adjustable operating parameter of the movable element in order to increase or decrease the intensity of the exercise and thereby increase or decrease an exerciser's heart rate into one of a plurality of target heart rate zones, wherein each of the plurality of target heart rate zones is calculated using both an average work heart rate and a recovery heart rate of the exerciser.

2. The exercise system of claim 1, further comprising a heart rate monitor that monitors the exerciser's heart rate.

3. The exercise system of claim 2, wherein the heart rate monitor is worn by the exerciser.

4. The exercise system of claim 1, wherein the controller calculates the plurality of target heart rate zones.

5. The exercise system of claim 1, wherein the plurality of target heart rate zones comprises four target heart rate zones.

6. The exercise system of claim 1, wherein the heart rate monitor communicates the exerciser's heart rate to the controller.

7. The exercise system of claim 1, wherein the exerciser's average work heart rate comprises the exerciser's average heart rate during a work portion of a fitness evaluation.

8. The exercise system of claim 1, wherein a lower limit of a first target heart rate zone of the plurality of target heart rate zones is calculated by subtracting 40% of the exerciser's recovery heart rate from the exerciser's average work heart rate, and wherein an upper limit of the first target heart rate zone is calculated by subtracting 30% of the exerciser's recovery heart rate from the exerciser's average work heart rate.

9. The exercise system of claim 1, wherein a lower limit of a second target heart rate zone of the plurality of target heart rate zones is calculated by subtracting 20% of the exerciser's recovery heart rate from the exerciser's average work heart rate, and wherein an upper limit of the second target heart rate zone is calculated by subtracting 15% of the exerciser's recovery heart rate from the exerciser's average work heart rate.

10. The exercise system of claim 1, wherein a lower limit of a third target heart rate zone of the plurality of target heart rate zones is calculated by subtracting 10% of the exerciser's recovery heart rate from the exerciser's average work heart rate, and wherein an upper limit of the third target heart rate zone is calculated by subtracting 5% of the exerciser's recovery heart rate from the exerciser's average work heart rate.

11. The exercise system of claim 1, wherein a lower limit of a fourth target heart rate zone of the plurality of target heart rate zones is calculated by adding 5% of the exerciser's recovery heart rate to the exerciser's average work heart rate, and wherein an upper limit of the fourth target heart rate zone is calculated by adding 10% of the exerciser's recovery heart rate to the exerciser's average work heart rate.

12. The exercise system of claim 1, wherein the exerciser's recovery heart rate is the difference between the exerciser's heart rate at the beginning and end of a recovery portion of a fitness evaluation.

13. The exercise system of claim 1, wherein the controller generates a series of program workouts using the plurality of target heart rate zones.

14. The exercise system of claim 13, wherein the series of program workouts may be designed to improve the exerciser's general fitness level, assist the exerciser in weight management, or improve the exerciser's performance in endurance sports.

15. The exercise system of claim 1, wherein the controller re-evaluates the exerciser's average work heart rate and recovery heart rate after a predetermined time period or after the exerciser has performed a predetermined number of workouts.

16. The exercise system of claim 15, wherein the controller recalculates the target heart rate zones based upon the exerciser's re-evaluated average work heart rate and recovery heart rate.

17. An exercise device that generates exercise program workouts for use with the exercise device, the exercise device comprising:
   a moveable element that is movable during the performance of exercise, the moveable element having one or more adjustable operating parameters;
   one or more processors; and
   one or more computer storage devices having stored thereon computer executable instructions that, when executed by the one or more processors:
   calculate an average work heart rate of an exerciser;
   calculate a recovery heart rate of the exerciser;
   calculate lower and upper limits of a plurality of target heart rate zones using both the average work heart rate and the recovery heart rate of the exerciser; and
   based upon a monitored heart rate of the exerciser, cause the one or more adjustable operating parameters of the moveable element to be adjusted in order to increase or decrease an intensity level of an exercise performed by the exerciser and thereby cause the exerciser's heart rate to increase or decrease into one of the plurality of target heart rate zones.

* * * * *